US009802840B2

(12) United States Patent
Shturm et al.

(10) Patent No.: US 9,802,840 B2
(45) Date of Patent: Oct. 31, 2017

(54) ULTRAVIOLET WATER DISINFECTION SYSTEM

(71) Applicant: Sensor Electronic Technology, Inc., Columbia, SC (US)

(72) Inventors: Igor Shturm, Columbia, SC (US); Saulius Smetona, Columbia, SC (US); Timothy James Bettles, Columbia, SC (US); Yuri Bilenko, Columbia, SC (US); Ignas Gaska, Columbia, SC (US); Alexander Dobrinsky, Loudonville, NY (US); Michael Shur, Latham, NY (US); Remigijus Gaska, Columbia, SC (US)

(73) Assignee: Sensor Electronic Technology, Inc., Columbia, SC (US)

(*) Notice: Subject to any disclaimer, the term of this patent is extended or adjusted under 35 U.S.C. 154(b) by 483 days.

(21) Appl. No.: 14/324,528

(22) Filed: Jul. 7, 2014

(65) Prior Publication Data

US 2015/0008167 A1 Jan. 8, 2015

Related U.S. Application Data

(60) Provisional application No. 61/843,498, filed on Jul. 8, 2013, provisional application No. 61/874,969, filed on Sep. 6, 2013.

(51) Int. Cl.
  *C02F 1/00* (2006.01)
  *C02F 1/32* (2006.01)
  (Continued)

(52) U.S. Cl.
  CPC ............. *C02F 1/325* (2013.01); *C02F 1/001* (2013.01); *G01N 21/33* (2013.01); *G01N 21/85* (2013.01);
  (Continued)

(58) Field of Classification Search
  CPC .. C02F 1/001; C02F 1/008; C02F 1/32; C02F 1/325; C02F 9/00; C02F 2209/001;
  (Continued)

(56) References Cited

U.S. PATENT DOCUMENTS 4,017,734 A * 4/1977 Ross .......................... A61L 2/10
250/431
4,141,830 A 2/1979 Last
(Continued)

FOREIGN PATENT DOCUMENTS

JP 2001205281 7/2001
JP 2007069097 3/2007

OTHER PUBLICATIONS

Wurtele et al., "Application of GaN-based ultraviolet-C light emitting diodes—UV LEDs—for water disinfection", Water Research 45, Jun. 15, 2011, p. 1481-1489.
(Continued)

*Primary Examiner* — Joseph Drodge
(74) *Attorney, Agent, or Firm* — LaBatt, LLC

(57) ABSTRACT

A solution for treating a fluid, such as water, is provided. An ultraviolet transparency of a fluid can be determined before or as the fluid enters a disinfection chamber. In the disinfection chamber, the fluid can be irradiated by ultraviolet radiation to harm microorganisms that may be present in the fluid. One or more attributes of the disinfection chamber, fluid flow, and/or ultraviolet radiation can be adjusted based on the transparency to provide more efficient irradiation and/or higher disinfection rates. In addition, various attributes of the disinfection chamber, such as the position of the inlet(s) and outlet(s), the shape of the disinfection chamber, and other attributes of the disinfection chamber can be (Continued)

utilized to create a turbulent flow of the fluid within the disinfection chamber to promote mixing and improve uniform ultraviolet exposure.

20 Claims, 14 Drawing Sheets

(51) Int. Cl.
  *C02F 9/00* (2006.01)
  *G01N 21/33* (2006.01)
  *G01N 21/85* (2006.01)
  *G01N 21/94* (2006.01)

(52) U.S. Cl.
  CPC .. *C02F 2201/326* (2013.01); *C02F 2201/328* (2013.01); *C02F 2201/3222* (2013.01); *C02F 2201/3226* (2013.01); *C02F 2201/3227* (2013.01); *C02F 2201/3228* (2013.01); *C02F 2209/001* (2013.01); *C02F 2209/005* (2013.01); *C02F 2209/05* (2013.01); *C02F 2209/11* (2013.01); *C02F 2209/40* (2013.01); *C02F 2303/04* (2013.01); *G01N 21/94* (2013.01)

(58) Field of Classification Search
  CPC ............ C02F 2209/005; C02F 2209/05; C02F 2209/11; C02F 2201/326; C02F 2201/32; C02F 2201/3222; C02F 2201/3226; C02F 2201/3227; C02F 2201/3228; C02F 2201/328; C02F 2303/04; C02F 2209/40; B01J 9/12; B01J 9/123; G01N 21/33; G01N 21/85; G01N 21/94
  USPC ......... 210/85, 93, 94, 96.1, 192, 259, 748.1; 250/432, 435–437; 422/24, 186.3
  See application file for complete search history.

(56) References Cited

U.S. PATENT DOCUMENTS

| | | | |
|---|---|---|---|
| 4,400,270 A * | 8/1983 | Hillman | A61L 2/10 210/103 |
| 4,752,401 A | 6/1988 | Bodenstein | |
| RE34,513 E | 1/1994 | Ellner | |
| 5,494,576 A | 2/1996 | Hoppe et al. | |
| 5,503,800 A | 4/1996 | Free | |
| 5,536,395 A * | 7/1996 | Kuennen | C02F 1/283 210/143 |
| 5,589,935 A * | 12/1996 | Biard | A47L 15/4297 134/113 |
| 6,235,191 B1 * | 5/2001 | Nakamura | C02F 1/325 210/138 |
| 6,607,668 B2 | 8/2003 | Rela | |
| 6,607,672 B2 | 8/2003 | Koslow et al. | |
| 6,669,838 B1 * | 12/2003 | Baarman | A61L 2/10 210/103 |
| 6,773,610 B2 | 8/2004 | Korin | |
| 6,974,958 B2 | 12/2005 | Gadgil et al. | |
| 7,029,587 B2 | 4/2006 | Andrews | |
| 7,217,933 B2 | 5/2007 | Gadgil et al. | |
| 7,364,654 B2 | 4/2008 | Schulz | |
| 7,476,870 B2 | 1/2009 | Hopaluk et al. | |
| 7,632,410 B2 * | 12/2009 | Heiss | C02F 9/00 210/143 |
| 7,691,265 B2 | 4/2010 | Snyder | |
| 7,713,496 B2 | 5/2010 | Harris | |
| 7,862,728 B2 | 1/2011 | Yencho | |
| 8,541,758 B1 * | 9/2013 | Filson, II | C02F 1/325 250/453.11 |
| 8,758,630 B1 | 6/2014 | Britenstine | |
| 2005/0163648 A1 * | 7/2005 | Liang | A61L 2/10 422/1 |
| 2006/0006332 A1 * | 1/2006 | Dragoi | A61L 2/08 250/336.1 |
| 2006/0131246 A1 * | 6/2006 | Ehlers | C02F 1/325 210/748.1 |
| 2006/0186059 A1 | 8/2006 | Saccomanno et al. | |
| 2006/0283810 A1 * | 12/2006 | Ciccone Pe Dee | C02F 1/325 210/748.12 |
| 2008/0061005 A1 | 3/2008 | Hopaluk et al. | |
| 2008/0095661 A1 * | 4/2008 | Kohler | A61L 9/20 422/20 |
| 2010/0209294 A1 | 8/2010 | Owen et al. | |
| 2010/0296971 A1 | 11/2010 | Gaska et al. | |
| 2011/0257788 A1 * | 10/2011 | Wiemers | B01D 61/022 700/267 |
| 2012/0138816 A1 * | 6/2012 | Duineveld | C02F 1/325 250/437 |
| 2013/0048545 A1 | 2/2013 | Shatalov et al. | |
| 2013/0270429 A1 | 10/2013 | Bilenko et al. | |
| 2013/0319925 A1 | 12/2013 | Yee et al. | |
| 2014/0202962 A1 | 7/2014 | Bilenko et al. | |
| 2014/0346370 A1 * | 11/2014 | Dobrinsky | A61L 2/10 250/433 |

OTHER PUBLICATIONS

Bohrerova et al., "Assessment of DNA damage and repair in Mycobacterium terrae after exposure to UV irradiation", Journal of Applied Microbiology, Nov. 13, 2005, p. 995-1001.
Bank et al., "Bactericidal Effectiveness of Modulated UV Light", Applied and Environmental Microbiology, Dec. 1990, vol. 56, No. 12, p. 3888-3889.
Greene et al., "Computational Fluid Dynamics Analysis of the Effects of Reactor Configuration on Disinfection Efficiency", Water Environment Research, vol. 78, No. 9, Sep. 2006, p. 909-919.
Linden et al., "Enhanced UV Inactivation of Adenoviruses under Polychromatic UV Lamps", Applied and Environmental Microbiology, Dec. 2007, p. 7571-7574.
Wu et al., "Fabrication of hydrophobic alumina aerogel monoliths by surface modification and ambient pressure drying", Applied Surface Science 256, Nov. 2010, p. 5973-5977.
Hijnen et al., "Inactivation credit of UV radiation for viruses, bacteria and protozoan (oo)cysts in water: A review", Water Research 40, (2006), Nov. 30, 2004, p. 3-22.
Bowker et al., "Microbial UV fluence-response assessment using a novel UV-LED collimated beam system", Water Research 45 (2011), Sep. 10, 2010, p. 2011-2019.
Wolfe, "Ultraviolet disinfixtion of potable water: Current technology and research needs", Environ. Scl. Technol., vol. 24, No. E, 1990, p. 768-773.
Science Applications International Corp., "Ultraviolet Light Disinfection Technology in Drinking Water Application—An Overview", Sep. 1996, 270 pages.
Vilhunen et al., "Ultraviolet light-emitting diodes in water disinfection", Environ. Sci. Pollut. Res. (2009), 16, p. 439-442.
Kano et al., "UV Technologies in Water Purification Systems", The R&D Notebook, Feb. 2003, 12 pages.
Lee, International Search Report and Written Opinion for International Application No. PCT/Us2012/052006, Jan. 3, 2013, 12 pages.
Drodge, J., U.S. Appl. No. 14/817,558, Office Action1, dated Jun. 28, 2017, 8 pages.

* cited by examiner

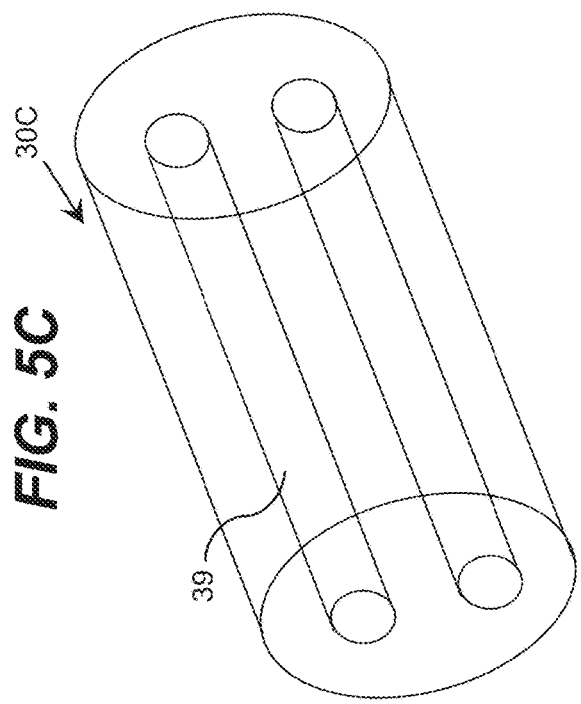
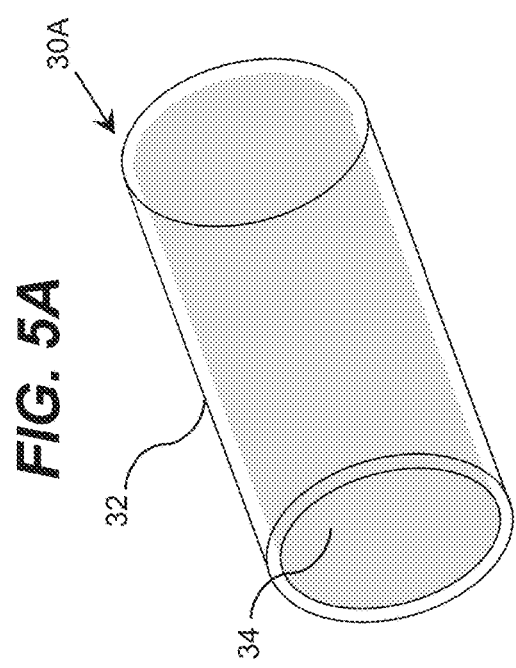
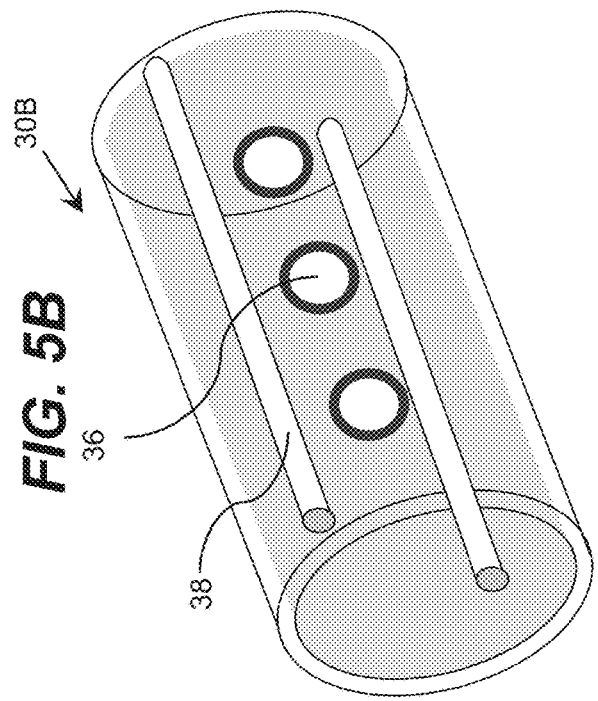

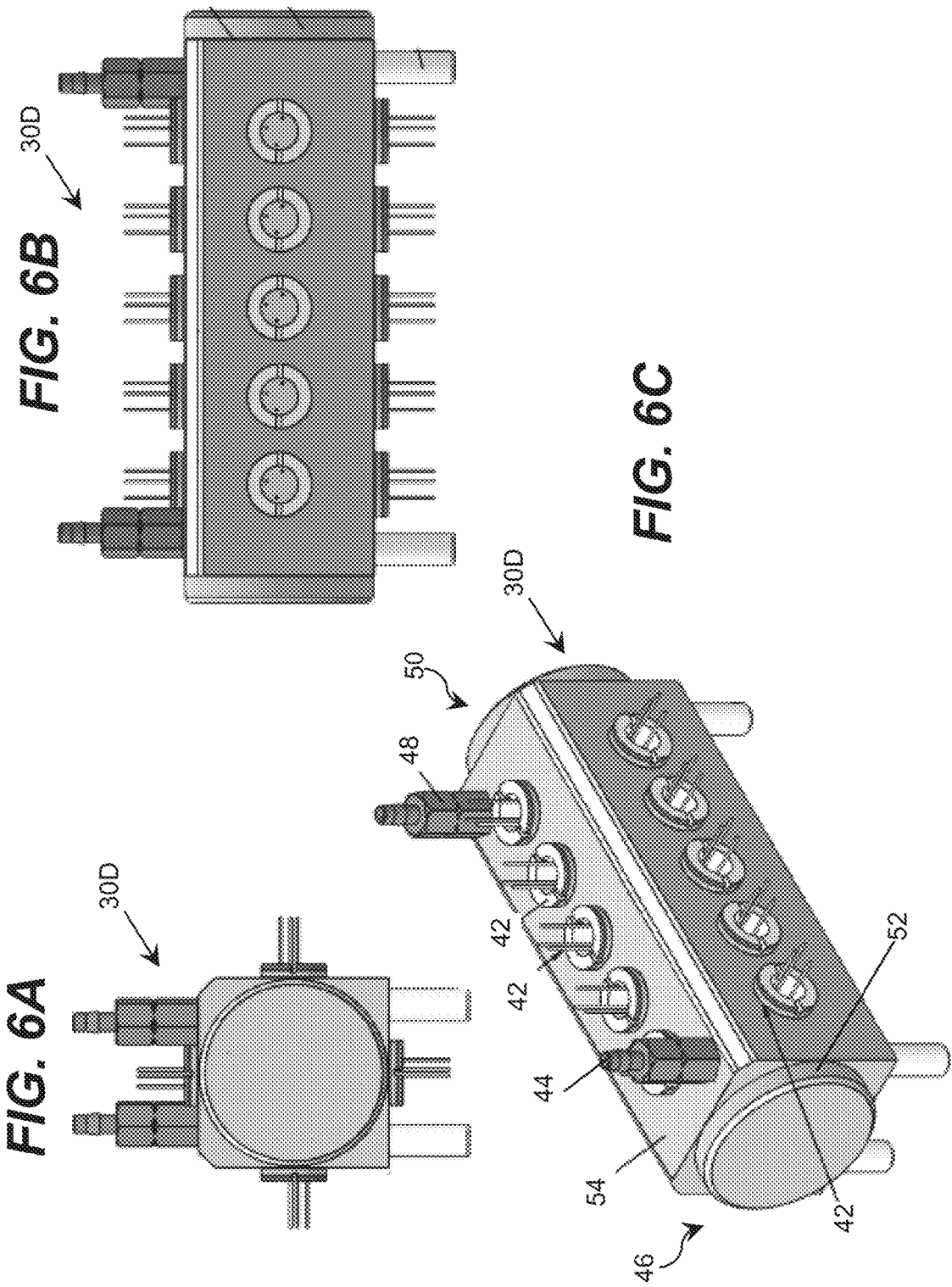

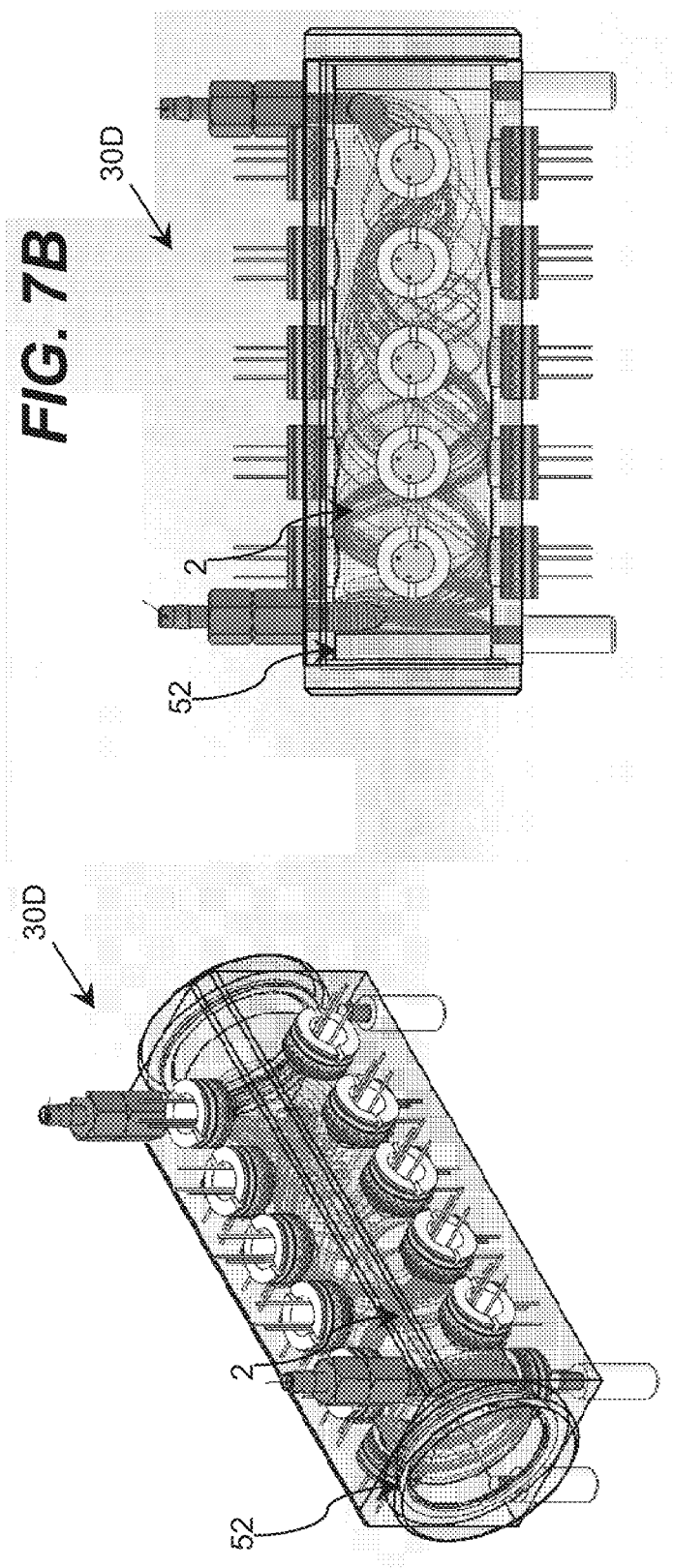

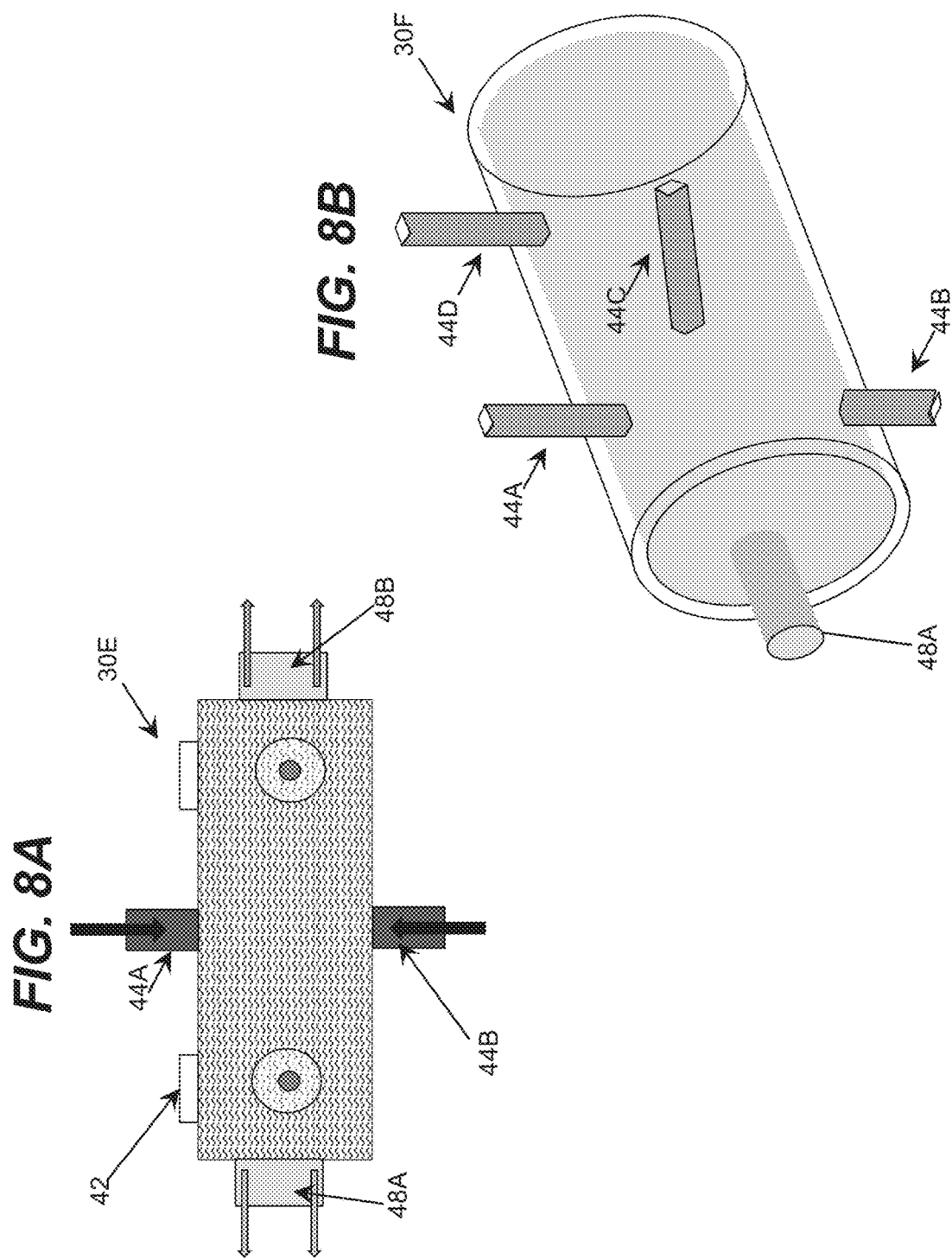

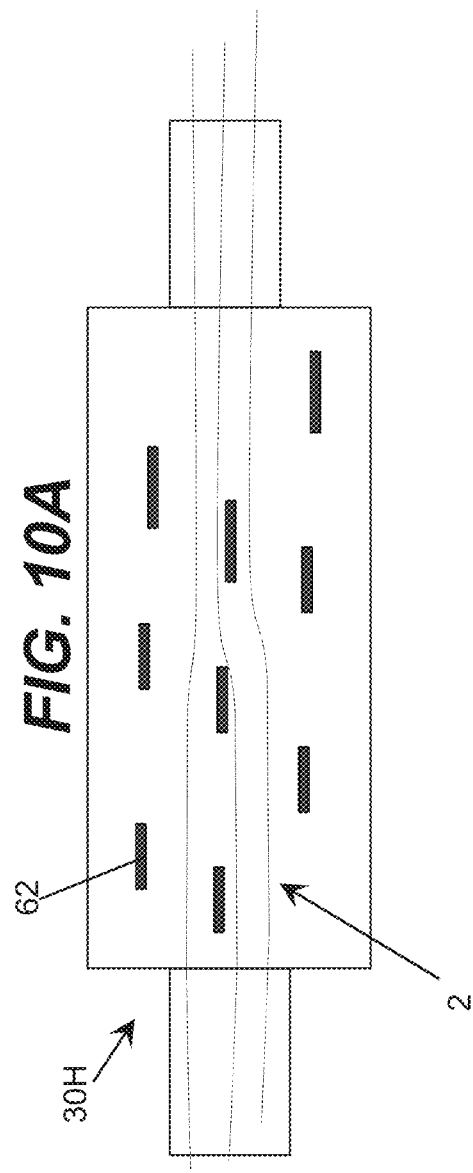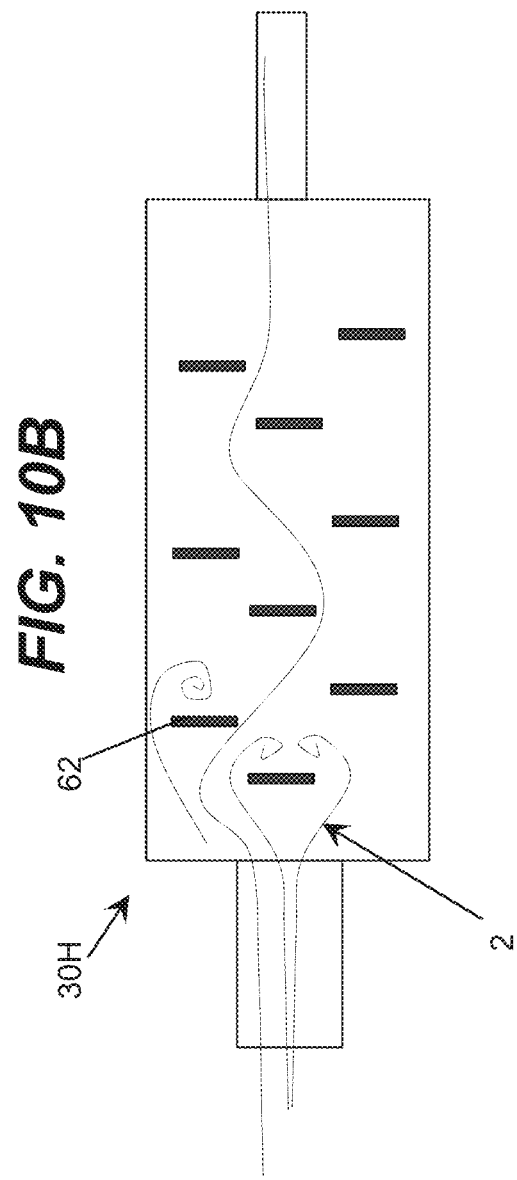

ULTRAVIOLET WATER DISINFECTION SYSTEM

REFERENCE TO RELATED APPLICATIONS

The current application claims the benefit of U.S. Provisional Application No. 61/843,498, titled "Ultraviolet Water Disinfection System," which was filed on 8 Jul. 2013, and U.S. Provisional Application No. 61/874,969, titled "Ultraviolet Water Disinfection System," which was filed on 6 Sep. 2014, both of which are hereby incorporated by reference. Aspects of the invention are related to co-pending U.S. patent application Ser. No. 13/591,728, which was filed on 22 Aug. 2012, and co-pending U.S. patent application Ser. No. 14/157,874, which was filed on 17 Jan. 2014, both of which are hereby incorporated by reference.

TECHNICAL FIELD

The disclosure relates generally to disinfection, and more particularly, to a solution for disinfecting a fluid, such as water, using deep ultraviolet light.

BACKGROUND ART

Water treatment using ultraviolet (UV) radiation offers many advantages over other forms of water treatment, such as chemical treatment. For example, treatment with UV radiation does not introduce additional chemical or biological contaminants into the water. Furthermore, ultraviolet radiation provides one of the most efficient approaches to water decontamination since there are no microorganisms known to be resistant to ultraviolet radiation, unlike other decontamination methods, such as chlorination. UV radiation is known to be highly effective against bacteria, viruses, algae, molds and yeasts. For example, hepatitis virus has been shown to survive for considerable periods of time in the presence of chlorine, but is readily eliminated by UV radiation treatment. The removal efficiency of UV radiation for most microbiological contaminants, such as bacteria and viruses, generally exceeds 99%. To this extent, UV radiation is highly efficient at eliminating *E-coli*, *Salmonella*, Typhoid fever, Cholera, Tuberculosis, Influenza Virus, Polio Virus, and Hepatitis A Virus.

Intensity, radiation wavelength, and duration of radiation are important parameters in determining the disinfection rate of UV radiation treatment. These parameters can vary based on a particular target culture. The UV radiation does not allow microorganisms to develop an immune response, unlike the case with chemical treatment. The UV radiation affects biological agents by fusing and damaging the DNA of microorganisms, and preventing their replication. Also, if a sufficient amount of a protein is damaged in a cell of a microorganism, the cell enters apoptosis or programmed death.

Ultraviolet radiation disinfection using mercury based lamps is a well-established technology. In general, a system for treating water using ultraviolet radiation is relatively easy to install and maintain in a plumbing or septic system. Use of UV radiation in such systems does not affect the overall system. However, it is often desirable to combine an ultraviolet purification system with another form of filtration since the UV radiation cannot neutralize chlorine, heavy metals, and other chemical contaminants that may be present in the water. Various membrane filters for sediment filtration, granular activated carbon filtering, reverse osmosis, and/or the like, can be used as a filtering device to reduce the presence of chemicals and other inorganic contaminants.

Mercury lamp-based ultraviolet radiation disinfection has several shortcomings when compared to deep ultraviolet (DUV) light emitting device (LED)-based technology, particularly with respect to certain disinfection applications. For example, in rural and/or off-grid locations, it is desirable for an ultraviolet purification system to have one or more of various attributes such as: a long operating lifetime, containing no hazardous components, not readily susceptible to damage, requiring minimal operational skills, not requiring special disposal procedures, capable of operating on local intermittent electrical power, and/or the like. Use of a DUV LED-based solution can provide a solution that improves one or more of these attributes as compared to a mercury vapor lamp-based approach. For example, in comparison to mercury vapor lamps, DUV LEDs: have substantially longer operating lifetimes (e.g., by a factor of ten); do not include hazardous components (e.g., mercury), which require special disposal and maintenance; are more durable in transit and handling (e.g., no filaments or glass); have a faster startup time; have a lower operational voltage; are less sensitive to power supply intermittency; are more compact and portable; can be used in moving devices; can be powered by photovoltaic (PV) technology, which can be installed in rural locations having no continuous access to electricity and having scarce resources of clean water; and/or the like.

FIGS. 1A-1C and FIGS. 2A-2B illustrate previous applications where the UV disinfection systems are based on mercury lamps. One of the important issues associated with mercury lamps is that it is difficult to turn on and off such a device rapidly. As such, the intensity levels of mercury lamp are sub-optimal for devices that require rapid turn-on/turn-off times. FIG. 2B further illustrates a mixing element for creating a turbulent flow in the device. The turbulent flow promotes mixing and improves radiation exposure of the fluid.

SUMMARY OF THE INVENTION

When treating fluid partially transparent to UV radiation, it is often desirable to: provide a mechanism for increasing transparency of the fluid; monitor transparency of the fluid; monitor the filtering system; provide a mechanism for mixing and circulating the flow, and/or the like, in order to yield sufficiently high UV radiation levels to deliver necessary UV radiation dose for the disinfection of microorganisms. Embodiments of the present invention address one or more of these issues.

Aspects of the invention provide a solution for treating a fluid, such as water. The solution can determine an ultraviolet transparency of a fluid before or as the fluid enters a disinfection chamber. In the disinfection chamber, the fluid can be irradiated by ultraviolet radiation to harm microorganisms that may be present in the fluid. One or more attributes of the disinfection chamber, fluid flow, and/or ultraviolet radiation can be adjusted based on the transparency to provide more efficient irradiation and/or higher disinfection rates. In addition, various attributes of the disinfection chamber, such as a position of an inlet and outlet, a shape of the disinfection chamber, and/or other attributes of the disinfection chamber, can be utilized to create a turbulent flow of the fluid within the disinfection chamber to promote mixing and improve uniform UV exposure.

A first aspect of the invention provides a system comprising: a disinfection chamber for disinfecting a fluid, the disinfection chamber comprising: an inner cylindrical chamber; at least one inlet located at a first end of the disinfection chamber and at least one outlet located at a second end of the disinfection chamber, wherein the at least one inlet and the at least one outlet are positioned to provide a rotational force to the fluid within the inner cylindrical chamber; and a set of ultraviolet radiation sources configured to emit ultraviolet radiation directed within the inner cylindrical chamber; a filtering system located at the at least one inlet of the disinfection chamber configured to filter the fluid; a sensing component located between the filtering system and the at least one inlet configured to evaluate a transparency of the fluid; and a control component configured to control at least one of: the set of ultraviolet radiation sources or a flow rate of the fluid at the at least one inlet, based on the transparency of the fluid.

A second aspect of the invention provides a system comprising: a disinfection chamber for disinfecting a fluid, the disinfection chamber comprising: an inner chamber; at least one inlet located at a first end of the disinfection chamber and at least one outlet located at a second end of the disinfection chamber, wherein the at least one inlet and the at least one outlet are both located on a top side of the disinfection chamber, such that fluid flowing through the at least one inlet and the at least one outlet has a rotational force within the inner chamber; and a set of ultraviolet radiation sources configured to emit ultraviolet radiation directed within the inner cylindrical chamber; a sensing component located adjacent to the at least one inlet configured to obtain sensing data corresponding to a transparency of the fluid; and a control component configured to determine the transparency of the fluid using the sensing data and control the set of ultraviolet radiation sources based on the transparency of the fluid.

A third aspect of the invention provides a system comprising: a planar disinfection chamber for disinfecting a fluid, the disinfection chamber comprising: at least one inlet and at least one outlet; a set of ultraviolet radiation sources located on a first side of the disinfection chamber; a set of scattering elements located on a second side of the disinfection chamber opposite the first side, the set of scattering elements configured to reflect ultraviolet radiation; and a plurality of wall barriers located within the disinfection chamber and extending from the first side to the second side, the plurality of wall barriers configured to provide a flow path for the fluid through the disinfection chamber; a sensing component located along the flow path for the fluid, the sensing component configured to obtain sensing data corresponding to a transparency of the fluid; and a control component configured to control the set of ultraviolet radiation sources based on the transparency of the fluid.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 5A-5C show illustrative disinfection chambers according to embodiments.

FIGS. 6A-6C show an illustrative disinfection chamber according to an embodiment.

FIGS. 7A and 7B show an illustrative disinfection chamber according to an embodiment.

FIGS. 8A and 8B show illustrative disinfection chambers including a plurality of inlets and a plurality of outlets according to an embodiment.

FIGS. 10A and 10B show an illustrative disinfection chamber including moveable blades according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for treating a fluid, such as water. The solution can determine an ultraviolet transparency of a fluid before or as the fluid enters a disinfection chamber. In the disinfection chamber, the fluid can be irradiated by ultraviolet radiation to harm microorganisms that may be present in the fluid. One or more attributes of the disinfection chamber, fluid flow, and/or ultraviolet radiation can be adjusted based on the transparency to provide more efficient irradiation and/or higher disinfection rates. In addition, various attributes of the disinfection chamber, such as a position of the inlet and outlet, a shape of the disinfection chamber, and/or other attributes of the disinfection chamber can be utilized to create a turbulent flow of the fluid within the disinfection chamber to promote mixing and improve uniform UV exposure. As used herein, unless otherwise noted, the term "set" means one or more (i.e., at least one) and the phrase "any solution" means any now known or later developed solution.

Aspects of the invention are designed to improve an efficiency with which ultraviolet radiation is absorbed by a fluid, such as water, by increasing the turbulent flow of the fluid within a disinfection chamber. The improved design can provide a higher disinfection rate while requiring less power by improving uniform UV exposure, making operation of the overall system more efficient. In a particular embodiment, the fluid is water and the system is configured to provide a reduction of microorganism (e.g., bacterial and/or viral) contamination in the water by at least a factor of two. In a more particular embodiment, the system provides approximately 99.9% decontamination of the water.

Figure 1C:
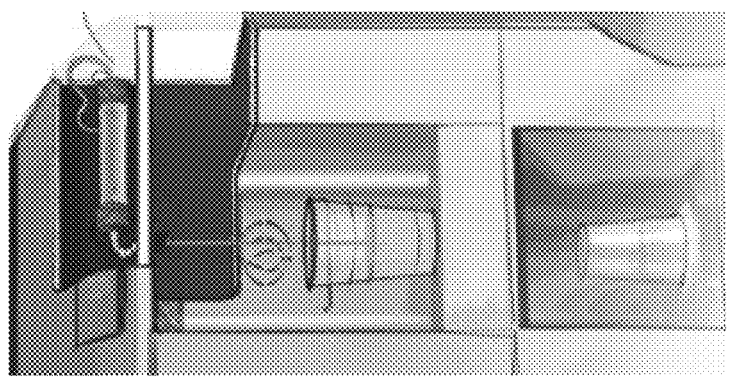
FIGS. 1A-1C show ultraviolet disinfection systems according to the prior art.
Figure 1B:
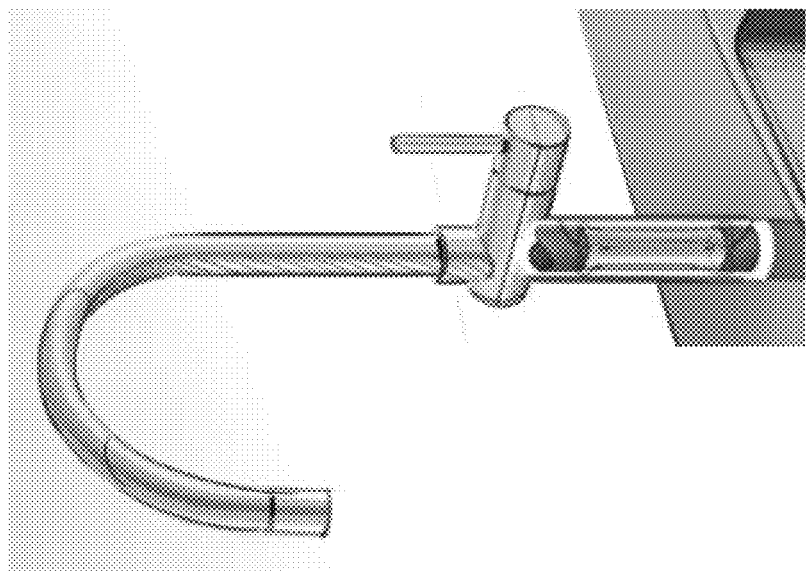
Figure 1A:
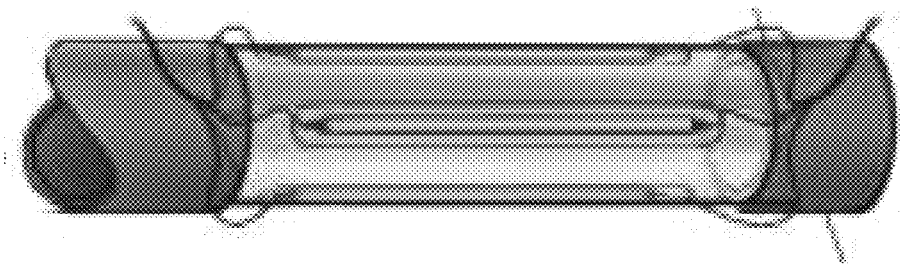
Figure 2A:
FIGS. 2A and 2B show ultraviolet disinfection systems according to the prior art.
Figure 2B:
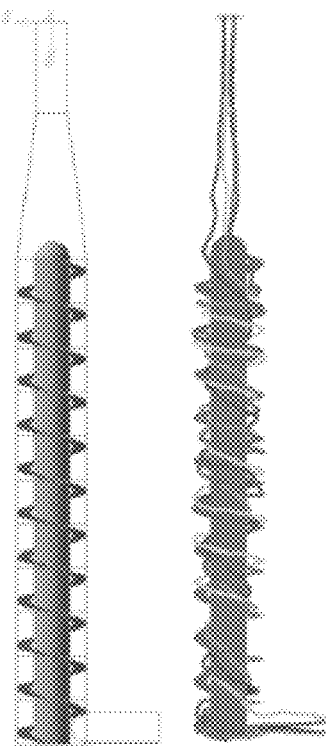
Figure 3:
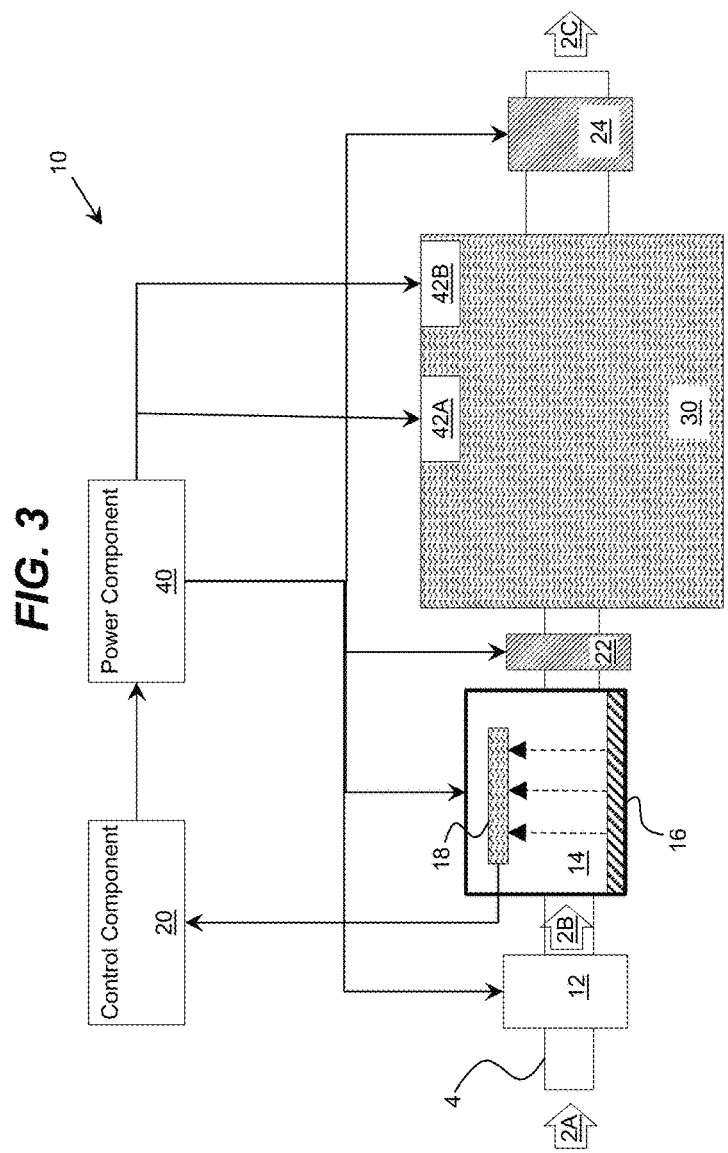
FIG. 3 shows an illustrative system for treating a fluid according to an embodiment.

Turning to the drawings, FIG. 3 shows an illustrative system 10 for treating a fluid 2A according to an embodiment. In particular, the system 10 includes a filtering unit 12 and a disinfection chamber 30. During operation of the system 10, unfiltered fluid 2A can enter the filtering unit 12 through an inlet of the filtering unit 12 and filtered fluid 2B can exit the filtering unit 12. As illustrated, the filtering unit 12 can be located along a fluid path 4 to the disinfection chamber 30 such that the filtered fluid 2B enters into the disinfection chamber 30 through an outlet of the filtering unit 12. In an embodiment, the inlet and outlet of the filtering unit 12 are permeable sides of the filtering unit 12, as illustrated. Furthermore, disinfected fluid 2C can exit the disinfection chamber 30 after being irradiated as described herein.

The fluid 2A-2C can comprise any type of fluid, including a liquid or a gas. In an embodiment, the fluid 2A-2C is water, which can be treated to make the water suitable for any desired human or animal interaction, e.g., potable. To this extent, as used herein, the terms "purification," "decontamination," "disinfection," and their related terms mean treating the fluid 2A-2C so that it includes a sufficiently low number of contaminants (e.g., chemical, sediment, and/or the like) and microorganisms (e.g., virus, bacteria, and/or the like) so that the fluid is safe for the desired interaction with a human or other animal. For example, the purification, decontamination, or disinfection of water means that the resulting water has a sufficiently low level of microorganisms and other contaminants so that a typical human or other animal can interact with (e.g., consume or otherwise use) the water without suffering adverse effects from microorganisms and/or contaminants present in the water. A target level of microorganisms and/or contaminants can be defined, for example, by a standards setting organization, such as a governmental organization.

The filtering unit 12 can comprise any combination of one or more of various types of filter materials and filtering solutions capable of removing one or more of various target contaminants (e.g., organic and/or inorganic compounds) that may be present in the fluid 2A as it passes there through. For example, the filtering unit 12 can comprise a sediment filter, which can comprise a filter material having a lattice structure, or the like, which is configured to remove target contaminants of a minimum size that may be present within the fluid 2A. Furthermore, the filtering unit 12 can comprise a filter material capable of removing one or more target contaminants by adsorption. For example, the filter material can comprise activated carbon, an ion exchange resin, or the like, and can be in the form of a ceramic, a block (e.g., carbon block), a granular fill, and/or the like. In this case, the filter material can remove various chemical contaminants, such as heavy metals, chlorine, and/or the like, which may be present in the fluid 2A. Regardless, it is understood that the filtering unit 12 can incorporate any combination of one or more filtering solutions including, for example, reverse osmosis, membrane filtration (e.g., nanofiltration), ceramic filtration, sand filtration, ultrafiltration, microfiltration, ion-exchange resin, and/or the like.

In any event, prior to entering the disinfection chamber 30, a sensing component 14 can evaluate a transparency level of the filtered fluid 2B. In an embodiment, the system 10 is configured to adjust one or more attributes of radiation emitted in the disinfection chamber 30 based on a transparency of the filtered fluid 2B to radiation of the target wavelength. To this extent, the sensing component 14 can be configured to acquire data corresponding to a transparency of the filtered fluid 2B. In particular, the sensing component 14 can be configured such that at least a portion of the filtered fluid 2B passes there through. Additionally, the sensing component 14 can include a set of radiation sources 16, which generate radiation of one or more target wavelengths directed toward a set of radiation sensors 18. In an embodiment, the set of radiation sources 16 includes at least one visible light emitting device and at least one ultraviolet light emitting device, while the set of radiation sensors 18 includes at least one visible light sensitive sensing device and at least one ultraviolet radiation sensitive sensing device. As illustrated, the sensing component 14 is located along the fluid path 4 for the fluid 2B and can comprise a housing having two open ends through which the filtered fluid 2B passes with a set of radiation sources 16 located on one side and a set of radiation sensors 18 located on the opposing side.

The set of radiation sensors 18 can provide transparency data corresponding to a transparency of the filtered fluid 2B as a set of inputs for a control component 20. Based on the set of inputs, the control component 20 can adjust one or more aspects of the operation of a set of ultraviolet sources 42A, 42B used to treat the filtered fluid 2B. The control component 20 can also base operation of the set of ultraviolet sources 42A, 42B on the flow rate of the fluid 2B entering the disinfection chamber 30. For example, the control component 20 can adjust one or more attributes of the power provided to the set of ultraviolet sources 42A, 42B by a power component 40. The power component 40 can be configured to independently or collectively adjust an amount of power provided to each ultraviolet source 42A, 42B. The power component 40 can be capable of delivering various energy levels of power to the ultraviolet sources 42A, 42B in a continuous and/or pulsed manner. In an embodiment, the control component 20 includes a computer system, which is configured to calculate an ultraviolet radiation absorption of the filtered fluid 2B based on the transparency data received from the set of radiation sensors 18. It is understood that an embodiment of the control component 20 can be configured to control the operation of one or more additional components, including the set of radiation sources 16, the set of radiation sensors 18, a mechanism (e.g., pump) for managing movement of the fluid 2A-2C, and/or the like. Similarly, an embodiment of the control component 20 can receive input data from one or more additional sensing devices, such as a flow rate sensor, a sensor indicating that the disinfection chamber 30 is closed, sensors indicating a disinfection level of the filtered fluid 2A and/or the disinfected fluid 2C, and/or the like.

Figure 4B:
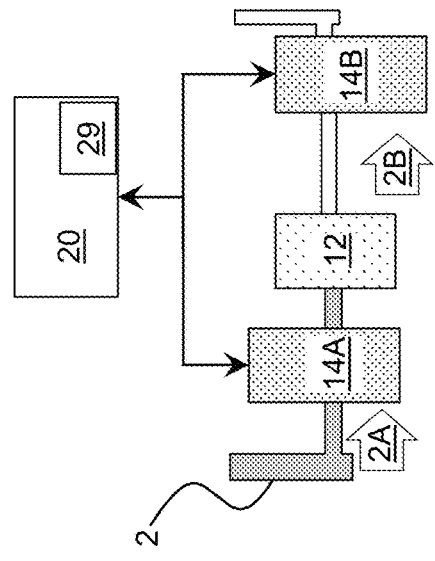
FIGS. 4A-4C shows illustrative fluid path configurations for a filtering unit and a sensing component for determining filter saturation according to an embodiment.
Figure 4C:
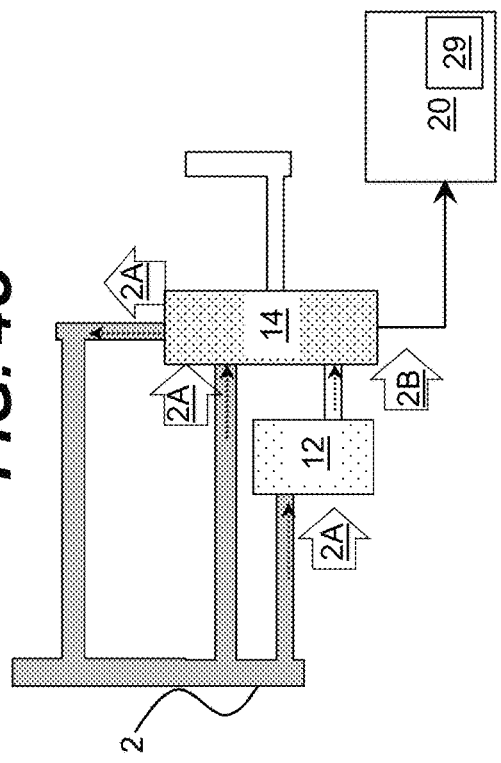
Figure 4A:
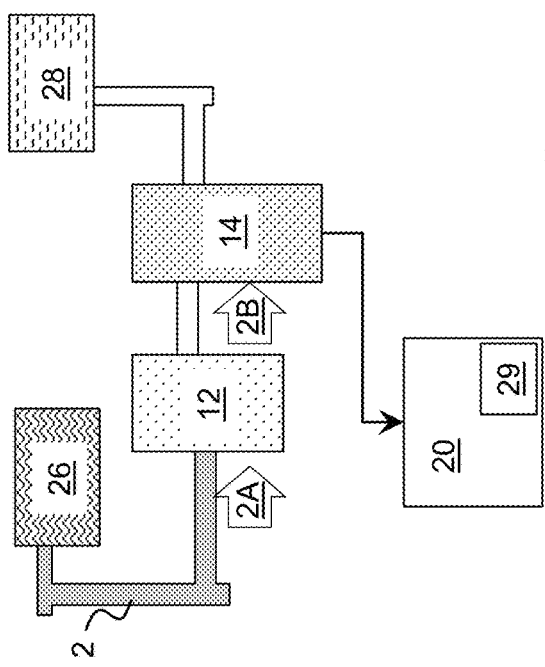

Although the fluid path 4 is shown as a linear flow path through the filtering unit 12 and the sensing component 14, it is understood that this is only one example of the possible configurations of the filtering unit 12 and the sensing component 14. For example, FIGS. 4A-4C show illustrative fluid path configurations for a filtering unit 12 and a sensing component 14 that can be used to determine a filter saturation according to an embodiment. Filter saturation indicates the efficiency of the filtering unit 12 by indicating the amount of contaminants that are contained by the filtering unit 12. The filter saturation can be based on the transparency level of the filtered fluid 2B. In an embodiment, as shown in FIG. 4A, a test fluid 2A with a known level of contaminants within a container 26 can be filtered through the filtering unit 12. A transparency level for the filtered fluid 2B can be measured by the sensing component 14 and the filtered fluid 2B can be stored in a container 28. The transparency data for the filtered fluid 2B can be provided as an input to the control component 20 and compared to the known level of contaminants of the test fluid 2A. If the filtering unit 12 fails to filter a predetermined percentage of the known contaminants in the test fluid 2A, the control component 20 can indicate that a filter saturation for the filtering unit 12 is reached. The control component 20 can include an alarm 29 (e.g., visual, auditory, and/or the like), which indicates that the filtering unit 12 should be replaced.

In another embodiment, as shown in FIG. 4B, when the fluid 2A contains an unknown amount of contaminants, a first transparency level for the unfiltered fluid 2A can be measured by a first sensing component 14A. A second transparency level for the filtered fluid 2B can be measured by a second sensing component 14B. The first and second transparency levels can be provided as inputs to the control component 20 and compared with one another to determine the efficiency of the filtering unit 12. If the filtering unit 12 fails to filter a predetermined percentage of contaminants within the unfiltered fluid 2A, the control component 20 can include an alarm 29, which indicates that the filtering unit 12 should be replaced.

In another embodiment, as shown in FIG. 4C, when the fluid 2A contains an unknown amount of contaminants, the sensing component 14 can include a first input for unfiltered fluid 2A and a second input for filtered fluid 2B. The sensing component 14 can measure a first transparency level for the unfiltered fluid 2A and a second transparency level for the filtered fluid 2B. This transparency data can be provided as inputs to the control component 20 to determine the efficiency of the filtering unit 12. If the filtering unit 12 fails to filter a required percentage of contaminants within the unfiltered fluid 2A, the control component 20 can include an alarm 29, which indicates that the filtering unit 12 should be replaced.

Returning to FIG. 3, in an embodiment, the ultraviolet sources 42A, 42B include a set of ultraviolet light emitting diodes (LEDs), each of which is configured to emit radiation having a peak wavelength within the ultraviolet range of wavelengths, i.e., between 400 nanometers (nm) and 100 nm. In a more particular embodiment, the ultraviolet radiation emitted by an ultraviolet LED comprises deep ultraviolet radiation having a peak wavelength below 300 nanometers (nm). In a still more particular embodiment, the ultraviolet radiation emitted by an ultraviolet LED has a peak wavelength in a range between approximately 250 nm and approximately 290 nm. In another embodiment, the ultraviolet radiation sources 42A, 42B include a plurality of ultraviolet LEDs having a plurality of distinct peak wavelengths within the deep ultraviolet range of wavelengths, which can improve germicidal efficiency for targeting a plurality of types of microorganisms that may be present in the filtered fluid 2B. The ultraviolet radiation can be introduced into the disinfection chamber 30 using any solution. For example, the ultraviolet sources 42A, 42B can comprise ultraviolet LEDs placed along an interior surface of a wall forming the disinfection chamber 30. Furthermore, waveguide structures, such as optical fiber, or the like, can be utilized to introduce ultraviolet radiation generated by an ultraviolet source located external of the disinfection chamber 30.

As different pathogens have various absorption wavelengths (for example, MS2 Phage has an absorption maxima at 271 nm, and *Escherichia coli* at 267 nm), an embodiment of the system 10 can include ultraviolet sources 42A, 42B operating at various wavelengths. For example, the disinfection chamber 30 can contain ultraviolet sources 42A, 42B containing phosphor and emitting at least some radiation at 250 nm wavelength, with the phosphor converting a portion (e.g., at least five percent) of the emitted UV radiation into ultraviolet radiation having a 280 nm wavelength. In addition, a peak wavelength of an ultraviolet source 42A, 42B can be chosen to provide a maximum absorption for a target pathogen. For instance, ultraviolet sources 42A, 42B with several wavelength spectra comprising wavelength maxima at 250, 260, 265, 270 and 280 nm, with a full width at half maximum (FWHM) of ten nm or twenty nm can be included in the system 10. More particular illustrative embodiments of configurations of the ultraviolet sources 42A, 42B include: at least two wavelength spectra having maxima at 265 nm and 250 nm with a FWHM of ten nm; at least two wavelength spectra having maxima at 250 nm and 270 nm with FWHM of ten nm; and at least two wavelength spectra having maxima at 260 nm and 280 nm and FWHM of twenty nm. During operation of the system 10, the control component 20 can operate all of the ultraviolet sources 42A, 42B or selectively operate only a subset of the ultraviolet sources 42A, 42B based on a set of target contaminants and their corresponding absorption wavelengths.

In an embodiment, the control component 20 operates the ultraviolet sources 42A, 42B in a pulsed manner. For example, the control component 20 can cause the power component 40 to provide pulsed electrical power to the ultraviolet sources 42A, 42B. A frequency of pulsation and the ultraviolet radiation intensity can be configured to provide a target amount of sterilization. The pulsed operation criteria can be determined in advance, e.g., by testing the disinfection chamber 30 for various contaminants and fluid 2B transparency levels and recording the frequency of pulsation, the intensity of pulsed ultraviolet light, and sterilization levels for each frequency/intensity value in a database stored in the control component 20. The time dependent pulsation and intensity adjustment does not have to be periodic, but can be aperiodic, contain pulses of different wavelengths and different intensities etc. The employed pulses can be from different ultraviolet sources 42A, 42B, and can include, for example, a combination of DUV LED(s), DUV laser(s), and/or DUV lamp(s).

The system 10 can also include a first sensor 22 and a second sensor 24 located along the fluid path 4 for the fluid 2A-2C at an inlet and an outlet of the disinfection chamber 30, respectively. The first sensor 22 can be configured to detect the disinfection level of the filtered fluid 2B, while the second sensor 24 can be configured to detect the disinfection level of the disinfected fluid 2C. The first and second sensors 22, 24 can provide this disinfection data as a set of inputs for the control component 20. Based on this disinfection data, the transparency data from the sensing component 14, and/or the flow rate of the filtered fluid 2B entering the disinfection chamber, the control component 20 can adjust the power to the ultraviolet sources 42A, 42B.

Sensors 22, 24 can comprise an ultraviolet fluorescence sensor, an ultraviolet absorbance sensor, and/or the like. The UV fluorescence sensor 22, 24 can acquire data corresponding to a scattering of UV radiation within the disinfection chamber 30. The control component 20 can process the data corresponding to the scattering of UV radiation to correlate it with a level of contamination in the filtered fluid 2B, and make any adjustments to the operation of the ultraviolet sources 42A, 42B accordingly. Similarly, the control component 20 can process data acquired by the sensor 22, 24 to maintain a target level of ultraviolet flux within the disinfection chamber 30.

The disinfection chamber 30 can include one or more attributes and/or mechanisms to improve the efficiency of the ultraviolet irradiation by introducing turbulent flow to the filtered fluid 2B to promote uniform UV exposure. To this extent, referring to FIGS. 5A-5C, illustrative disinfection chambers 30A, 30B, 30C according to embodiments are shown. A disinfection chamber can be formed by multiple cylindrical chambers inserted into one another to promote UV radiation recirculation. In an embodiment, as shown in FIG. 5A, an outer chamber 32 can comprise UV reflective material that is at least 70% diffusive reflectance to UV light in the range of 230 nanometers (nm) to 360 nm at radiation angles normal to the surface, while the inner chamber 34 can comprise UV transparent material that is at least 40% transparent to the UV radiation in the range of 230 nm to 360 nm at radiation angles normal to the surface. The UV reflective material (e.g., mirror) of the outer chamber 32 can provide increased scattering of the ultraviolet radiation within the disinfection chamber 30 and a reduced loss of ultraviolet radiation from the disinfection chamber 30. For example, the walls of the outer chamber 32 can comprise a reflective material, such as an aluminum-based material, such as alumina, which has a relatively high reflectivity coefficient for ultraviolet radiation. The UV reflective material can also include a membrane of expanded polytetrafluoroethylene (ePTFE), such as GORE® diffuse reflector product (DRP) material, or the like. A UV diffusive material can also be used, such as polytetrafluoroethylene (e.g., Teflon offered by DuPont Co.), that is capable of diffusive reflectance. The inner chamber 34 can be formed of any type of material that is UV transparent, such as fused silica, sapphire, and/or the like.

The outer chamber 32 and inner chamber 34 can be separated by a low index of refraction material. The low index of refraction layer of material between the outer chamber 32 and the inner chamber 34 can be formed of any type of material having a lower index of refraction than the filtered fluid 2B, including: aerogel; a composite material comprising, for example, a layer of air and a thin layer of fused silica; and/or the like. Inclusion of the low refraction layer will cause the ultraviolet radiation to be totally internally reflected (TIR) at an interface between the filtered fluid 2B and the low refraction layer for rays of ultraviolet radiation propagating at angles to the interface normal that are greater than TIR angles. The additional layer between the outer chamber 32 and the inner chamber 34 can be partially transparent and partially reflective and contain voids (e.g., micropores, or achieved via patterning) to control the refractive index of the middle layer. Although it is not shown, the outer chamber 32 and/or the inner chamber 34 can include a patterned roughness and/or grooves to promote light scattering and reflection of the UV radiation using any solution. The patterned roughness and/or grooves may be formed by means of hot embossing, pattern imprinting, lithography, and/or the like. In FIG. 5B, the disinfection chamber 30B can include various UV sources. For example, the chamber 30B is shown including UV LEDs 36 and UV lamps 38.

In any of the disinfection chambers, a metallic material of the chamber walls can include a coating, such as polytetrafluoroethylene (PTFE), fluorinated ethylene-propylene (FEP), perfluoroalkoxy (PFA), various Teflons, and/or the like, to prevent corrosion. The coating can be applied by, for example, spray deposition or plasma deposition. The coating should be partially transparent and/or partially reflective and can have relatively low UV light absorbing characteristics. For example, the coating on the chamber walls should not absorb more than approximately 60% of the light radiated in the normal surface direction at wavelengths between 230 nanometers (nm) and 360 nm.

In another embodiment, the fluid can flow through partially transparent liners, such as liners 39 shown in the disinfection chamber 30C in FIG. 5C. The fluid flows through the liners 39 and does not interact with walls of the disinfection chamber 30C or with the UV sources 42A, 42B (FIG. 3), which prevents corrosion from occurring. The partially transparent coating can also act as an anti-fouling coating, to prevent biofilm growth within the chamber. The transparency of the liner 39 can be at least 30% to the normal incident of UV light. The liners 39 can comprise a high performance polymer such as Teflon, PTFE, FEP, and/or the like. In an embodiment, the liners 39 can include a composite multilayer material with layers including high performance polymers.

Referring now to FIGS. 6A-6C, an illustrative disinfection chamber 30D according to an embodiment is shown. As best seen in FIG. 6C, the inner chamber 52 is a cylindrical pipe, while the outer chamber 54 is a rectangular shape. However, it is understood that the outer chamber 54 can comprise any shape around the inner chamber 52. The outer chamber 54 can contain electronic and/or mechanical components for the system 10 (FIG. 3), such as the control component 20, the power component 40, ultraviolet sources 42A, 42B, and/or the like. The inner chamber 52 can comprise a UV reflective material (e.g., mirror). Further, it is understood that the inner chamber 52 can comprise any cylinder. That is, as used herein, the term "cylinder" means a volume shape having an axial direction enclosed by a surface and by two planes perpendicular to the axial direction, which are located at each end of the volume shape. The length of the cylinder is defined as a distance between these two perpendicular planes. The two planes perpendicular to such axial direction are identified as a first and second end 46, 50.

Although it is not shown, it is understood that a filtering unit 12, sensors 22, 24, a sensing component 14, and/or the like, can be present within the outer chamber 54 of the disinfection chamber 30D. The inlet 44 is located at a first end 46 of the disinfection chamber 30D and the outlet 48 is located at a second end 50 of the disinfection chamber 30D. It is understood that the inlet 44 and outlet 48 do not have to be located directly on the surface of the perpendicular planes of the first end 46 and second end 50, respectively. In an embodiment, the inlet 44 is located proximate to the first end 46 of the inner cylindrical chamber 52, while the outlet 48 is located proximate to the second end 50 of the inner cylindrical chamber 52. In a more specific embodiment, the inlet 44 and the outlet 48 are located on the surface of the cylinder 52 within at least ten percent of the entire chamber length to the first and second ends 46, 50, respectively. Furthermore, a distance between the inlet 44 and the outlet 48 should not exceed approximately one half of the length of the inner cylindrical chamber 52. In an embodiment, the inlet 44 and the outlet 48 are positioned to provide a rotational force to the fluid within the disinfection chamber 30D. Referring now to FIGS. 7A and 7B, the rotational motion of the fluid 2 within the inner chamber 52 is shown. The rotational motion promotes mixing of the fluid and increases UV exposure. Returning to FIGS. 6A-6C, the inner chamber 52 can include cylindrical coordinates r, z, θ, where r is the radial coordinate of the cylindrical pipe, z is the distance along the pipe axis, and θ is the angular position along the arc. The UV sources 42 can be positioned around the inner chamber 52 at angle θ being 0 degrees, 90 degree, 180 degrees, and 270 degrees, all along the z axis.

Referring now to FIGS. 8A and 8B, illustrative disinfection chambers 30E, 30F including a plurality of inlets and a plurality of outlets according to an embodiment are shown. An increase in the number of inlets to a disinfection chamber can increase the turbulence level of the fluid within the disinfection chamber 30E, 30F and promote mixing of the fluid to increase UV exposure. The disinfection chamber 30E in FIG. 8A includes a first inlet 44A and a second inlet 44B. The first and second inlets 44A, 44B are positioned opposite one another and directed towards one another, so that the force of the fluid flowing in from the first inlet 44A against the force of the fluid flowing in from the second inlet 44B creates vorticity and mixing of the fluid within the chamber 30E. In an embodiment, the largest component of the flow velocity of the first or second inlets 44A, 44B is directed towards the other of the first or second inlets 44A, 44B. The first and second inlets 44A, 44B can be generally directed towards the same area, so that the flows from the inlets 44A, 44B collide and interact with one another during operation of the disinfection chamber 30E. In a more specific embodiment, the first inlet 44A is directly opposite of a second inlet 44B. However, it is understood that it is not necessary for the first inlet 44A to be directly opposite from the second inlet 44B and any relative arrangement can be utilized to cause interaction between the fluid flows.

In another embodiment, shown in FIG. 8B, the disinfection chamber 30F can include a plurality of inlets 44A-44D at any position along the disinfection chamber 30F. It is understood that a disinfection chamber can include any number of inlets. Further, any number of the inlets may be inactivated by the control component 20 (FIG. 3) and/or the flow of the fluid from the inlet can be controlled by the control component 20 (via, e.g., a valve). The control component 20 can control the number of activated inlets and/or the flow of the fluid from each of the inlets based upon the type of fluid that is being disinfected within the disinfection chamber. For example, highly transparent fluids may require a few large cross sectional inlets to provide a low level of turbulence, while highly opaque fluids may require multiple small cross-sectional inlets to provide high levels of turbulence.

Figure 9B:
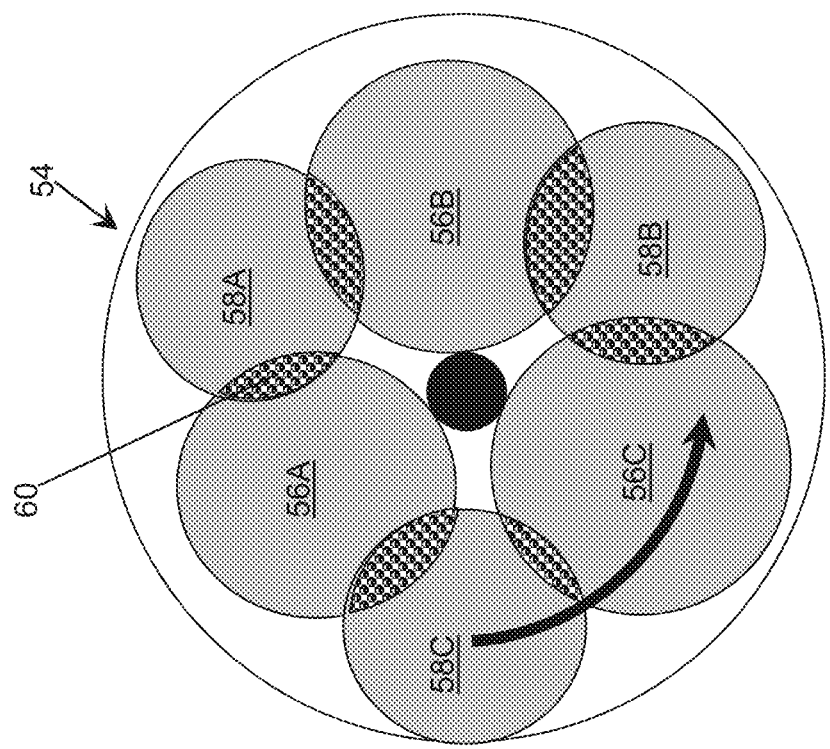
FIGS. 9A and 9B show an illustrative disinfection chamber including a plurality of inlets with variable diameter according to an embodiment.
Figure 9A:
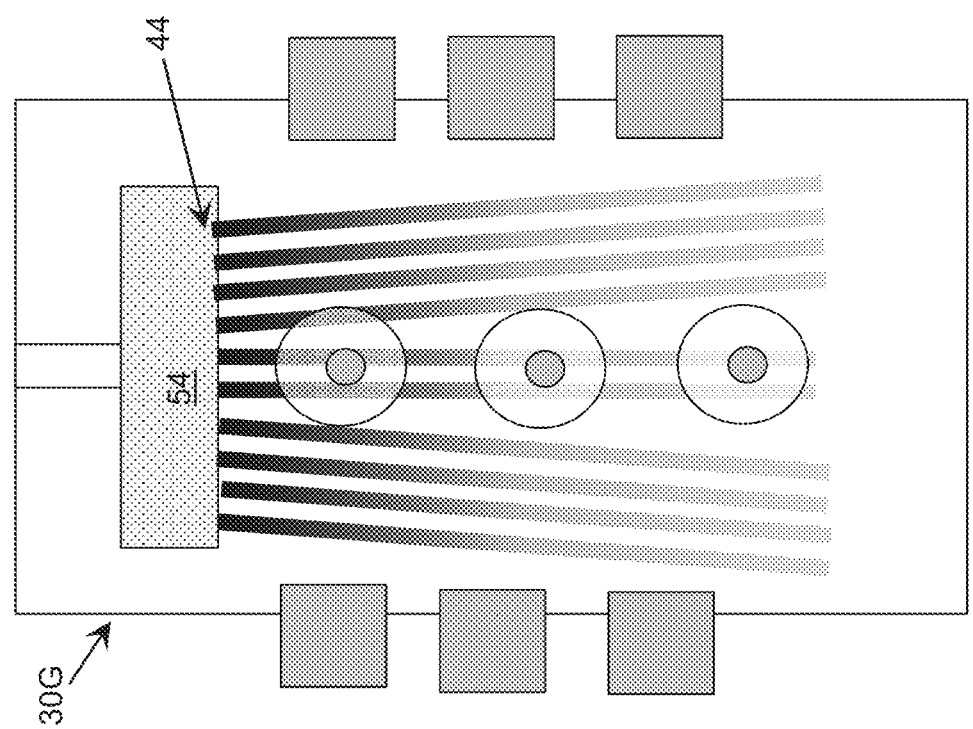

Referring now to FIG. 9A, an illustrative disinfection chamber 30G including a plurality of inlets 44 according to an embodiment is shown. The plurality of inlets 44 can be located on an inflow assembly 54. The plurality of inlets 44 on the inflow assembly 54 can deliver the fluid into the disinfection chamber 30F in multiple streams. Turning to FIG. 9B, in another embodiment, the inflow assembly 54 can include multiple levels of inlets. For example, the inflow assembly 54 can include a first level of inlets 56A-56C and a second level of inlets 58A-58C. Although only two levels are shown, it is understood that the inflow assembly 54 can include more levels of inlets. The levels of inlets in inflow assembly 54 can rotate, so that the fluid flows through the areas of overlap 60 between the first level of inlets 56A-56C and the second level of inlets 58A-58C. The control component 20 can rotate the levels of inlets to control the size of the areas of overlap 60 and can change the flow of the fluid. Therefore, changing the size of the area of overlap 60 can modify the level of turbulence provided to the fluid in the disinfection chamber 30F.

In an embodiment, a disinfection chamber can include one or more mechanisms within the disinfection chamber to alter the flow path of the fluid to increase the turbulence of the fluid. For example, in FIGS. 10A and 10B, an illustrative disinfection chamber 30H including a plurality of moveable blades 62 according to an embodiment is shown. In FIG. 10A, the plurality of moveable blades 62 are positioned to be linear with the fluid flow path 2. In FIG. 10B, the plurality of moveable blades 62 are positioned to be orthogonal to the fluid flow path 2, which disrupts the fluid flow path 2 and increases the turbulence of the fluid. The increase in fluid turbulence promotes fluid mixing and increases UV exposure. The plurality of moveable blades 62 can be controlled by the control component 20 (FIG. 3). The control component 20 can adjust each moveable blade 62 independently and can adjust each of the plurality of moveable blades 62 to produce a desired turbulence in the fluid flow 2 based on the flow rate of the fluid, the type of fluid, the disinfection level of the fluid, the transparency of the fluid, and/or the like.

Figure 11:
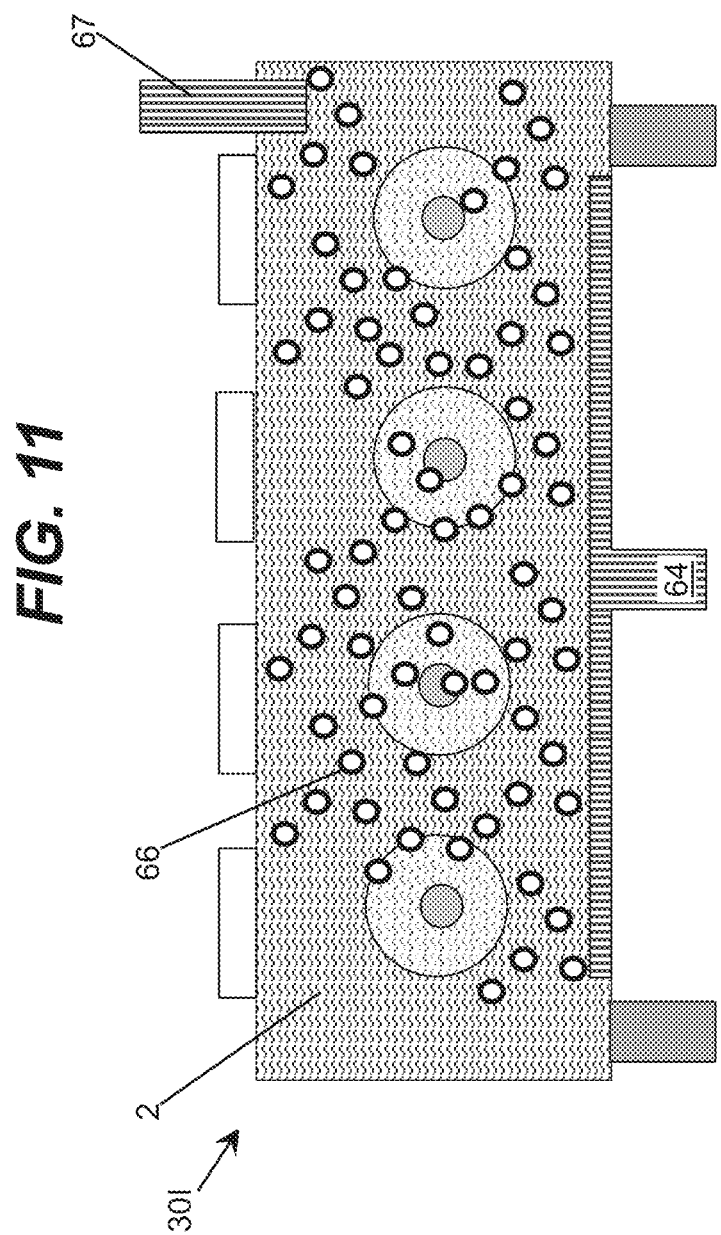
FIG. 11 shows an illustrative disinfection chamber including a gas chamber according to an embodiment.

Further improvement of increasing UV exposure for fluids, such as semi-opaque fluids with an absorption coefficient in the range of approximately 0.0001-10 $cm^{-1}$, can be achieved by including a gas phase in the fluid in the disinfection chamber. For example, the control component 20 can introduce a gas phase into the fluid, which introduces a transparent phase in the fluid and promotes the propagation of UV radiation throughout the semi-opaque fluid. The interface of the fluid and the gas also can increase light scattering. In an embodiment, a disinfection chamber 30I as shown in FIG. 11 can include a gas chamber 64 for providing a gas phase (e.g., bubbles 66) to the fluid 2. The gas chamber 64 can include an air feeder, pump, and/or the like, for introducing a gas phase to the fluid 2. Although the gas chamber 64 is shown located on one side of the disinfection chamber 30I, it is understood that the gas chamber 64 can be located on any side of the disinfection chamber 30I. The gas chamber 64, in general, can be positioned along the disinfection chamber 30I to promote propagation of the bubbles 66 by the use of gravity. In another embodiment, the gas chamber 64 can be placed in a location including lower UV radiation. The control component 20 (FIG. 3) can control the amount of bubbles 66 introduced to the fluid via the gas chamber 64 based upon the transparency of the fluid (by using sensing component 14 in FIG. 3). The disinfection chamber 30I can include a vent 67 for collecting and venting out the bubbles 66 from the chamber 30I.

Figure 12A:
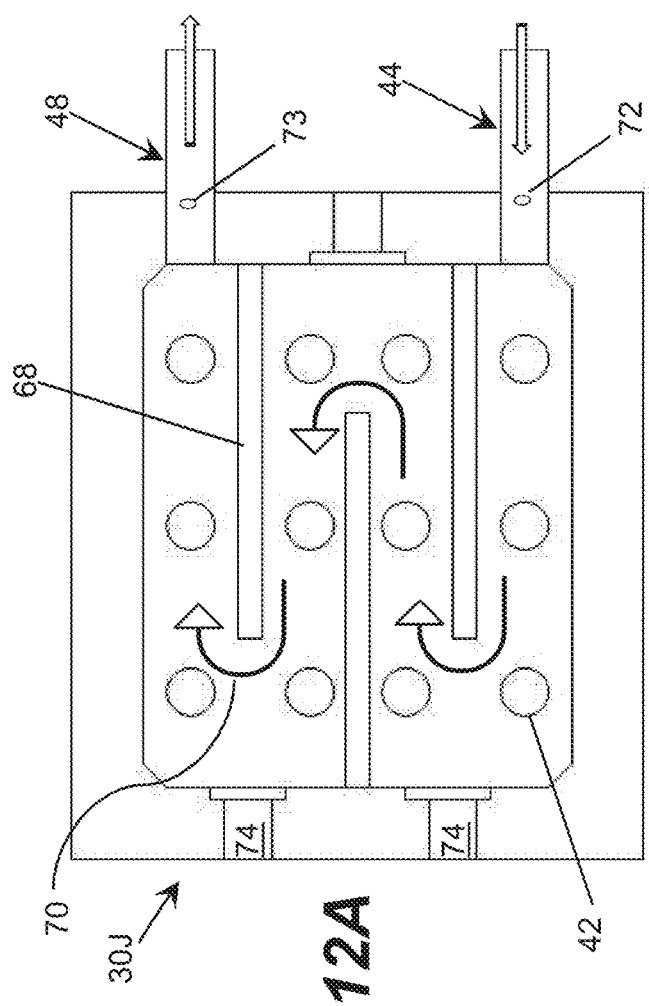
FIGS. 12A and 12B show an illustrative system for treating a fluid according to another embodiment.
Figure 12B:
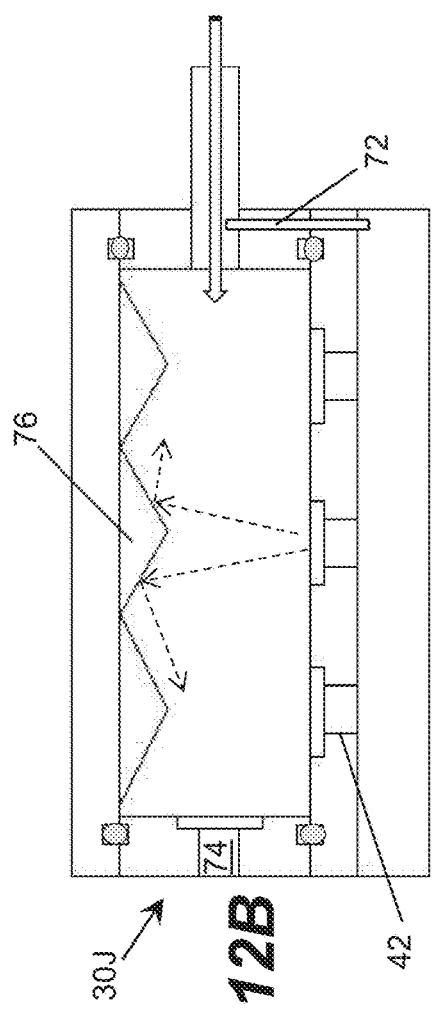

In an embodiment, the fluid can have a low ultraviolet transparency and be highly absorbent of UV radiation. As a result, a distribution of ultraviolet light throughout the fluid can be utilized to provide a more efficient disinfection. FIGS. 12A and 12B shows an illustrative planar disinfection chamber 30J including a plurality of wall barriers 68 used to create a complex flow path for the fluid according to an embodiment. Certain aspects of the system 10 (FIG. 3), such as the filtering unit 12, the sensors 22, 24, and/or the like, are not shown in FIGS. 12A and 12B for clarity. The plurality of wall barriers 68 are configured to cause filtered fluid 2B (FIG. 3) to flow in a serpentine path 70 through the disinfection chamber 30J. A plurality of ultraviolet sources 42 are located along the serpentine path 70, which emit ultraviolet radiation into the filtered fluid 2B in various locations as the filtered fluid 2B flows along the path 70. UV detectors 74 are located along the path 70 to evaluate a transparency level of the fluid 2B, which can be processed to determine the efficiency of the disinfection system as the fluid 2B flows through the disinfection chamber 30J. In order to determine whether the fluid is properly mixed, a conductivity tracer injector 72 can be located at each inlet 44 and a conductivity sensor 73 can be located at each outlet 48. The conductivity tracer injector 72 injects a timed pulse of a conductivity tracer, such as a salt solution, and/or the like, into the fluid. The conductivity sensor 73 can measure a conductivity of the fluid as a function of time to determine the concentration of salt in the fluid. The concentration of salt can be used to determine how well the fluid is mixed throughout the corresponding chamber 30J.

Figure 13A:
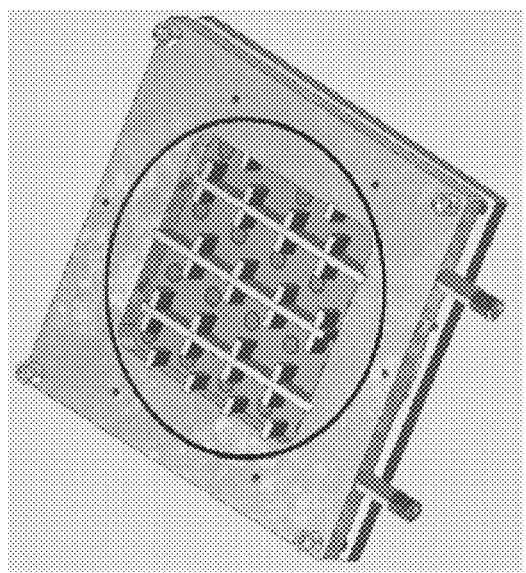
FIGS. 13A and 13B show perspective views of an illustrative system for treating a fluid according to an embodiment.
Figure 13B:
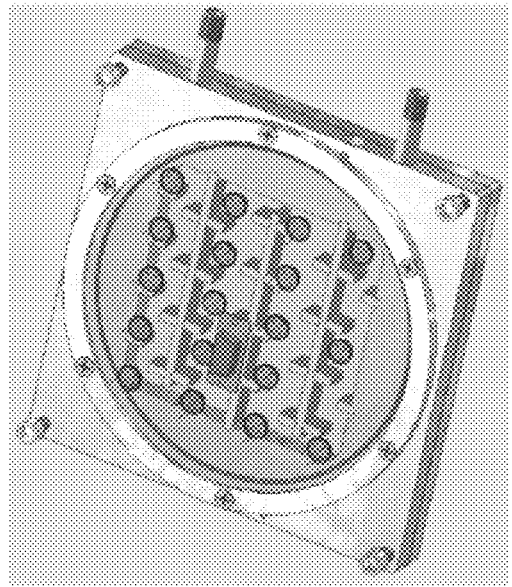

In an embodiment, the planar disinfection chamber 30J can include a plurality of scattering elements to promote uniform distribution of the UV radiation. Referring now to FIG. 12B, a side view of the planar disinfection chamber 30J is shown. The UV sources 42 are located on a first side of the disinfection chamber 30J and a plurality of scattering elements 76 are located on a second side of the disinfection chamber 30J, opposite of the UV sources 42. The UV sources 42 can radiate UV radiation to the fluid within the disinfection chamber 30J through windows (not shown) comprising a transparent material, such as sapphire, quartz, and/or the like. FIGS. 13A and 13B show perspective top and bottom views, respectively, of the disinfection chamber 30J for treating a fluid according to an embodiment.

Figure 14:
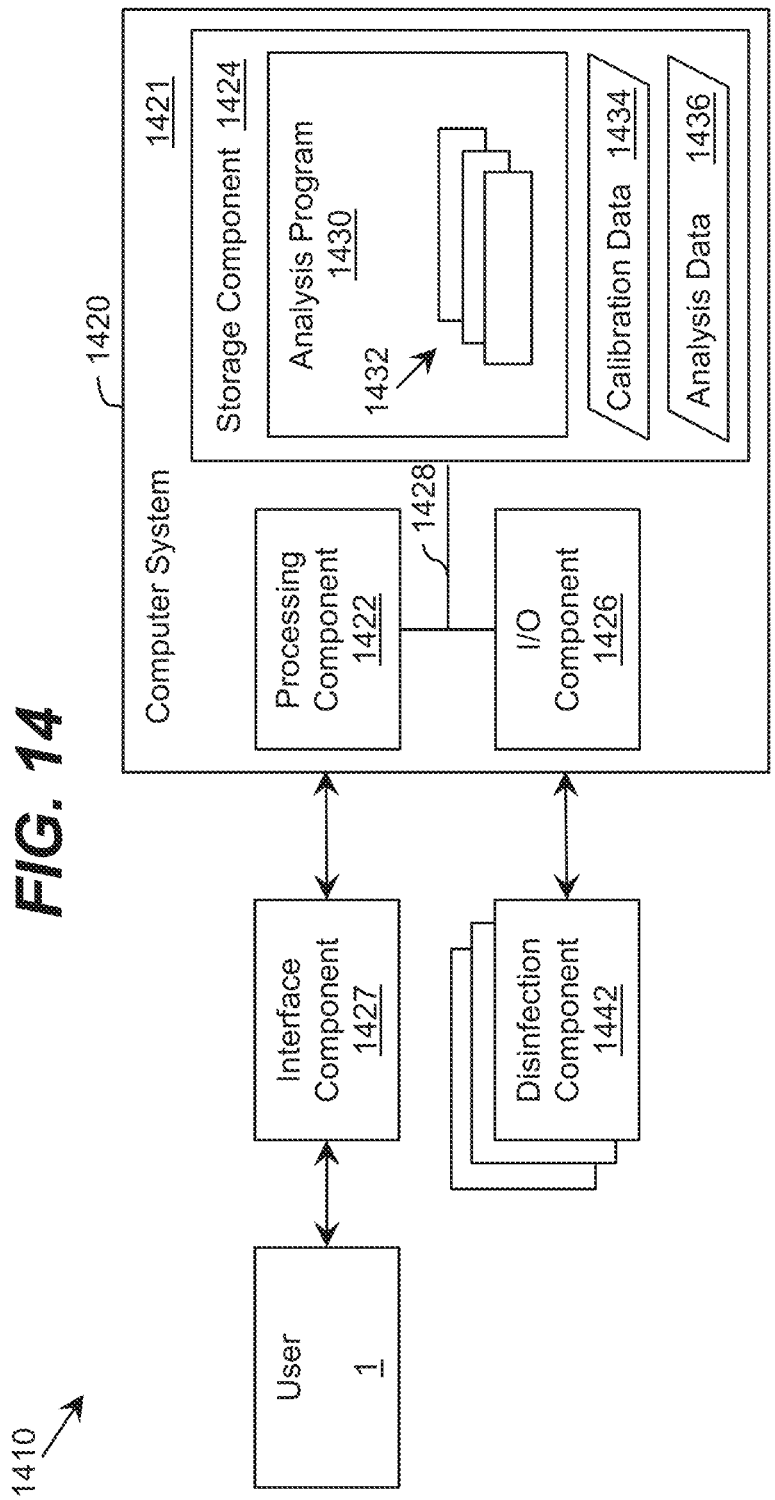
FIG. 14 shows an illustrative disinfection system according to an embodiment.

As described herein, a control component 20 can operate one or more components of a disinfection system 10 to disinfect a fluid. FIG. 14 shows an illustrative disinfection system 1410 according to an embodiment. In this case, the system 1410 includes a monitoring and/or control component 1420, which is implemented as a computer system 1421 including an analysis program 1430, which makes the computer system 1421 operable to manage a set of disinfection components 1442 (e.g., a power component, ultraviolet (UV) source(s), sensor(s), valves, movable blades, etc.) by performing a process described herein. In particular, the analysis program 1430 can enable the computer system 1421 to operate the disinfection components 1442 and process data corresponding to one or more conditions of the chamber and/or a fluid present in the chamber.

In an embodiment, during an initial period of operation, the computer system 1421 can acquire data regarding one or more attributes of the fluid and generate analysis data 1436 for further processing. The analysis data 1436 can include information on the presence of one or more contaminants in the fluid, a transparency of the fluid, and/or the like. The computer system 1421 can use the analysis data 1436 to generate calibration data 1434 for controlling one or more aspects of the operation of the disinfection components 1442 by the computer system 1421 as discussed herein.

The computer system 1421 is shown including a processing component 1422 (e.g., one or more processors), a storage component 1424 (e.g., a storage hierarchy), an input/output (I/O) component 1426 (e.g., one or more I/O interfaces and/or devices), and a communications pathway 1428. In general, the processing component 1422 executes program code, such as the analysis program 1430, which is at least partially fixed in the storage component 1424. While executing program code, the processing component 1422 can process data, which can result in reading and/or writing transformed data from/to the storage component 1424 and/or the I/O component 1426 for further processing. The pathway 1428 provides a communications link between each of the components in the computer system 1421. The I/O component 1426 and/or the interface component 1427 can comprise one or more human I/O devices, which enable a human user 1 to interact with the computer system 1421 and/or one or more communications devices to enable a system user 1 to communicate with the computer system 1421 using any type of communications link. To this extent, during execution by the computer system 1421, the analysis program 1430 can manage a set of interfaces (e.g., graphical user interface(s), application program interface, and/or the like) that enable human and/or system users 1 to interact with the analysis program 1430. Furthermore, the analysis program 1430 can manage (e.g., store, retrieve, create, manipulate, organize, present, etc.) the data, such as calibration data 1434 and analysis data 1436, using any solution.

In any event, the computer system 1421 can comprise one or more general purpose computing articles of manufacture (e.g., computing devices) capable of executing program code, such as the analysis program 1430, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 1430 can be embodied as any combination of system software and/or application software.

Furthermore, the analysis program 1430 can be implemented using a set of modules 1432. In this case, a module 1432 can enable the computer system 1421 to perform a set of tasks used by the analysis program 1430, and can be separately developed and/or implemented apart from other portions of the analysis program 1430. When the computer system 1421 comprises multiple computing devices, each computing device can have only a portion of the analysis program 30 fixed thereon (e.g., one or more modules 1432). However, it is understood that the computer system 1421 and the analysis program 1430 are only representative of various possible equivalent monitoring and/or control systems 1420 that may perform a process described herein. To this extent, in other embodiments, the functionality provided by the computer system 1421 and the analysis program 1430 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 1420 can be implemented without any computing device, e.g., using a closed loop circuit implementing a feedback control loop in which the outputs of one or more disinfection components 1442 (e.g., sensing devices) are used as inputs to control the operation of one or more other disinfection components 1442 (e.g., UV LEDs).

Regardless, when the computer system 1421 includes multiple computing devices, the computing devices can communicate over any type of communications link. Furthermore, while performing a process described herein, the computer system 1421 can communicate with one or more other computer systems, such as the user 1, using any type of communications link. In either case, the communications link can comprise any combination of various types of wired and/or wireless links; comprise any combination of one or more types of networks; and/or utilize any combination of various types of transmission techniques and protocols.

While shown and described herein as a method and system for treating (e.g., disinfecting) a fluid, it is understood that aspects of the invention further provide various alternative embodiments. For example, in one embodiment, the invention provides a computer program fixed in at least one computer-readable medium, which when executed, enables a computer system to treat a fluid as described herein. To this extent, the computer-readable medium includes program code, such as the analysis program 1430, which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 1430, which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for treating a fluid. In this case, the generating can include configuring a control component 1420, such as the computer system 1421, to implement the method of treating a fluid as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
a disinfection chamber for disinfecting a fluid, the disinfection chamber comprising:
an inner cylindrical chamber;
at least one inlet located at a first end of the disinfection chamber and at least one outlet located at a second end of the disinfection chamber, wherein the at least one inlet and the at least one outlet are positioned to provide a rotational force to the fluid within the inner cylindrical chamber;
a set of ultraviolet radiation sources configured to emit ultraviolet radiation directed within the inner cylindrical chamber; and
an outer chamber surrounding the inner cylindrical chamber, wherein the outer chamber includes an ultraviolet diffusive reflective material and the inner cylindrical chamber includes an ultraviolet transparent material, and wherein the inner cylindrical chamber and the outer chamber are separated by a low index of refraction layer;
a filtering system located at the at least one inlet of the disinfection chamber configured to filter the fluid;
a sensing component located between the filtering system and the at least one inlet configured to evaluate a transparency of the fluid prior to entering the disinfection chamber; and
a control component configured to control at least one of: the set of ultraviolet radiation sources or a flow rate of the fluid at the at least one inlet, based on the transparency of the fluid.

2. The system of claim 1, wherein at least the at least one inlet is positioned at a non-zero angle with respect to a normal direction of a surface of the inner cylindrical chamber.

3. The system of claim 1, wherein an index of refraction of the low index of refraction layer is less than an index of refraction of the fluid entering the disinfection chamber.

4. The system of claim 1, wherein an interior wall of the inner chamber includes ultraviolet diffusive reflective material.

5. The system of claim 4, wherein the interior wall of the inner cylindrical chamber includes a patterned roughness surface.

6. The system of claim 1, wherein the disinfection chamber comprises a plurality of inlets and a plurality of outlets.

7. The system of claim 6, wherein a first inlet is located opposite of a second inlet such that fluid entering from the first inlet or the second inlet is directed towards the other of the first inlet or the second inlet and results in a turbulent fluid flow during fluid recombination from the first inlet and the second inlet.

8. The system of claim 6, wherein each inlet of the plurality of inlets includes a variable diameter, and the control component is configured to control the variable diameter of each inlet based on the transparency and a disinfection of the fluid.

9. The system of claim 1, wherein the disinfection chamber further comprises movable blades configured to control the flow of the fluid within the disinfection chamber.

10. The system of claim 1, further comprising a gas chamber adjacent to the disinfection chamber, the gas chamber configured to deliver a plurality of air bubbles into the fluid.

11. A system comprising:
a disinfection chamber for disinfecting a fluid, the disinfection chamber comprising:
an inner chamber;
at least one inlet located at a first end of the disinfection chamber and at least one outlet located at a second end of the disinfection chamber, wherein the at least one inlet and the at least one outlet are both located on a top side of the disinfection chamber, such that fluid flowing through the at least one inlet and the at least one outlet has a rotational force within the inner chamber; and a set of ultraviolet radiation sources configured to emit ultraviolet radiation directed within the inner cylindrical chamber;

a sensing component located adjacent to the at least one inlet configured to obtain sensing data corresponding to a transparency of the fluid prior to entering the disinfection chamber; and a control component configured to determine the transparency of the fluid using the sensing data and control the set of ultraviolet radiation sources based on the transparency of the fluid.

12. The system of claim 11, further comprising a filtering system located upstream from the at least one inlet of the disinfection chamber configured to filter the fluid, wherein the control component further comprises an alarm system configured to indicate a filter saturation based on the transparency of the fluid.

13. The system of claim 11, wherein the inner chamber includes a patterned surface of ultraviolet reflective material.

14. The system of claim 11, wherein the disinfection chamber comprises a plurality of inlets configured to create turbulence in a flow of the fluid within the inner chamber.

15. The system of claim 11, wherein the disinfection chamber further comprises movable blades configured to control the flow of the fluid within the inner chamber.

16. The system of claim 11, further comprising a gas chamber adjacent to the disinfection chamber, the gas chamber configured to deliver a plurality of air bubbles into the fluid.

17. A system comprising:

a planar disinfection chamber for disinfecting a fluid, the disinfection chamber comprising:

at least one inlet and at least one outlet;

a set of ultraviolet radiation sources located on a first side of the disinfection chamber;

a set of scattering elements located on a second side of the disinfection chamber opposite the first side, the set of scattering elements configured to reflect ultraviolet radiation; and a plurality of wall barriers located within the disinfection chamber and extending from the first side to the second side, the plurality of wall barriers configured to provide a flow path for the fluid through the disinfection chamber;

a sensing component located along the flow path for the fluid, the sensing component configured to obtain sensing data corresponding to a transparency of the fluid; and a control component configured to control the set of ultraviolet radiation sources based on the transparency of the fluid.

18. The system of claim 17, wherein the plurality of wall barriers include ultraviolet diffusive reflective material.

19. The system of claim 17, wherein the sensing component includes at least one ultraviolet detector.

20. The system of claim 17, further comprising a conductivity tracer injector located at the at least one inlet and a conductivity sensor located at the at least one outlet.

* * * * *

UNITED STATES PATENT AND TRADEMARK OFFICE
CERTIFICATE OF CORRECTION

PATENT NO. : 9,802,840 B2
APPLICATION NO. : 14/324528
DATED : October 31, 2017
INVENTOR(S) : Igor Shturm et al.

It is certified that error appears in the above-identified patent and that said Letters Patent is hereby corrected as shown below:

In the Specification

Column 1, Lines 10 and 11 "which was filed on 6 Sep. 2014" should read – which was filed on 6 Sep. 2013 –.

Signed and Sealed this
Fifth Day of December, 2017

Joseph Matal
*Performing the Functions and Duties of the
Under Secretary of Commerce for Intellectual Property and
Director of the United States Patent and Trademark Office*